United States Patent [19]

Thomas

[11] Patent Number: 5,188,618
[45] Date of Patent: Feb. 23, 1993

[54] THROMBUS-MOBILIZING THORACOSTOMY TUBE

[76] Inventor: Bruce W. Thomas, 304-D Queensdale, York, Pa. 17403

[21] Appl. No.: 695,468

[22] Filed: May 3, 1991

[51] Int. Cl.⁵ .......................................... A61M 25/00
[52] U.S. Cl. .................................... 604/267; 604/269
[58] Field of Search ................ 604/96, 99, 266–269, 604/323, 326

[56] References Cited

U.S. PATENT DOCUMENTS

| | | | |
|---|---|---|---|
| 726,009 | 4/1903 | Whisler | 446/220 |
| 1,549,790 | 8/1925 | Neusella | 446/220 |
| 2,230,138 | 1/1941 | Ewart | 446/220 |
| 3,331,371 | 7/1967 | Rocchi et al. | 604/96 |
| 3,635,220 | 1/1972 | Elcaness | 604/268 |
| 3,863,641 | 2/1975 | Popa | 604/267 |
| 4,227,533 | 10/1980 | Godfrey | 604/266 X |
| 4,240,433 | 12/1980 | Bordow | 604/96 X |
| 4,244,377 | 1/1981 | Grams | 128/742 |
| 4,301,797 | 11/1981 | Pollack | 604/266 X |
| 4,994,033 | 2/1991 | Shockey et al. | 604/101 |
| 5,049,132 | 9/1991 | Shaffer et al. | 604/101 |
| 5,085,636 | 2/1992 | Burns | 604/99 |

FOREIGN PATENT DOCUMENTS 0118763 7/1983 Japan ................................ 604/266

Primary Examiner—John D. Yasko
Assistant Examiner—Adam J. Cemak
Attorney, Agent, or Firm—Richard C. Litman

[57] ABSTRACT

A thrombus-mobilizing thoracostomy tube includes fenestrations to enable drainage when introduced into a thoracic cavity, the tube including a balloon which may be inflated to dislodge and move blood clots, the balloon being connected to a first tube to enable a suitable fluid to be introduced to inflate the balloon progressively from a distal end to a proximal end, and a second tube parallel to said first tube to enable the introduction of a flushing fluid into the thoracostomy tube, whereby blood clots may be dislodged and removed from the thoracostomy tube without removing any portion of the thoracostomy tube from the user's body, thereby substantially reducing the risk of contamination while maintaining sterile conditions. The flushing fluid may include a heparin solution, a saline solution, a heparinized saline fluid, or a urokinase fluid.

9 Claims, 2 Drawing Sheets

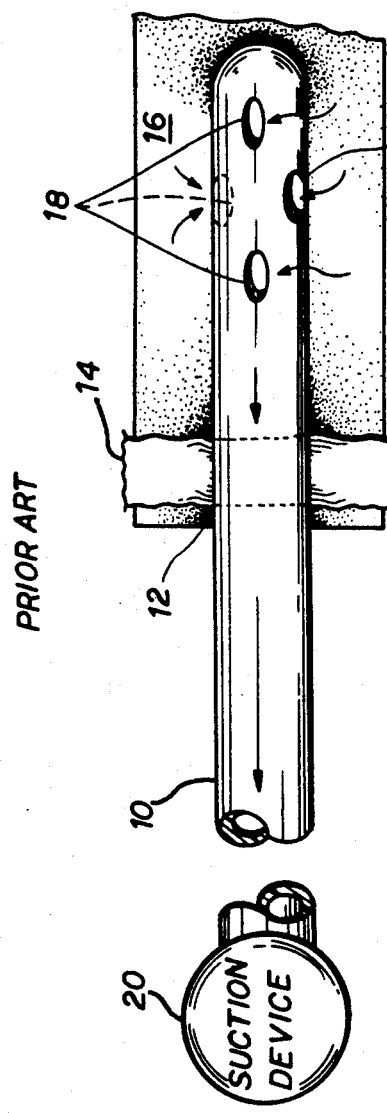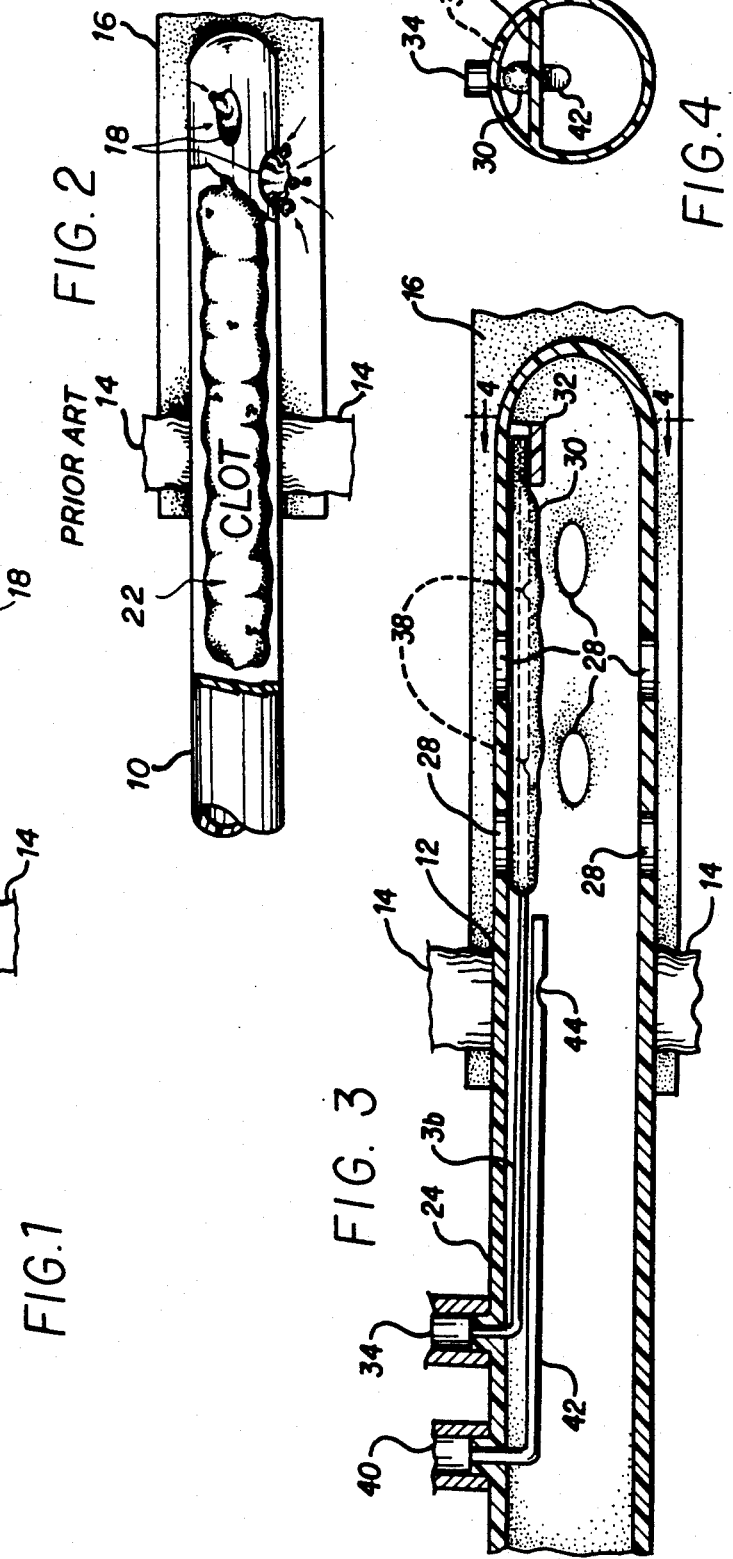

THROMBUS-MOBILIZING THORACOSTOMY TUBE

BACKGROUND OF THE INVENTION

1. Field of the Invention

This invention relates to a thoracostomy tube enabling dislodgment of blood clots which may form within the tube during drainage without the need to expose any portion of the tube which has been inserted into the thorax area of the body to the outside atmosphere, thereby avoiding the introduction of bacteria or other infectious agents into the body after removing the clot and maintaining sterile conditions.

Intrathoracic bleeding occurs with any form of chest injury that disrupts the tissues. In most instances of penetrating or non-penetrating trauma the blood is shed into the pleural cavity, often with some degree of pneumothorax.

From accumulated military and civilian experience, it can be estimated that slightly more than 10 percent of patients with traumatic hemothorax will require thoracostomy for control of bleeding or determination of the extent of injury. A progressive hemothorax or continued bleeding at the rate of more than 100 ml/hour beyond a few hours after placement of an intercostal catheter suggests bleeding from an intercostal artery, the internal thoracic artery, or a source that will require operative control.

Movement of the diaphragm and thoracic structures causes partial defibrination of blood that is shed into the pleural cavity, and clotting is usually incomplete. Sufficient coagulation does occur to interfere with efficient drainage of the pleural blood through intercostal catheters, and the latter often become plugged with a blood clot. Unless the pleural space is drained adequately, the transudation of fluid into the space can produce significant compression of the lung and a shift of the mediastinum toward the opposite hemothorax.

When the hemothorax exceeds an amount that fills the costophrenic sulcus, or when there is an associated pneumothorax, one or more large catheters should be placed in the pleural cavity. Drainage alone may be sufficient, but low suction applied to the catheters is often helpful when combined with active efforts at stripping the tubes of blood clots.

With a major hemothorax the success of tube drainage is often frustrated by extensive clotting which obstructs the tubes. A nonfunctioning chest tube represents a liability to the patient because of discomfort and the risk of carrying infection from the skin wound into the pleural area.

Especially with penetrating trauma, a hemothorax that fails to drain adequately through intercostal catheters may develop into empyema. An additional hazard is the organization of residual clot to form a fibrothorax. Although the incidence of these complications is not high, the consequences are severe, and it is wiser to proceed with thoracostomy and evacuation of the hemothorax before an extensive decortication becomes necessary.

In addition to traumatic causes of hemothorax, iatrogenic hemothoraces are induced during cardiac and coronary bypass surgery, and virtually always require thoracostomy tube drainage. Such surgery provides a major area for the application of the thrombus-mobilizing chest tube.

Further information about traumatic hemothorax may be found on page 630 of Principles of Surgery, 4th edition, by S.I. Schwartz, published in New York by McGraw-Hill in 1984.

2. Description of Related Prior Art

In a conventional thoracostomy tube which lacks any means for actively stripping a blood clot from the tube, the tube must be removed from the thoracic area before dislodging the blood clot from the tube. When the tube is removed even partially it is exposed to bacteria or other contaminants, thereby increasing the risk of infection when the tube is reinserted.

A number of devices are known in the prior art for stripping catheters of blood clots. U.S. Pat. No. 3,863,641 issued Feb. 4, 1975 to Loan Pop D. Popa discloses one such device for a catheter comprising a transparent elastic tube 1 having a plurality of orifices a, an inflatable balloonet 4 which acts as a piston, a mandrel 3 for moving balloonet 4, and a rigid tube 10 used to introduce liquid flushing material such as a heparin solution into tube 1. In the single figure, when a blood clot has formed, balloonet 4 is moved vertically in tube 1 to a position above orifices a by means of mandrel A, pushing the blood clot ahead of balloonet 4 while blocking access to orifices a by the liquid flushing material introduced into tube 1 through tube 10. Since at least a portion of mandrel 3 is moved outside of tube 1, mandrel 3 is exposed to a variety of contaminants which are introduced into the body when the balloonet 4 is returned to its initial position at the distal end of tube 1, thereby increasing the risk of infection. U.S. Pat. No. 4,228,802 issued Oct. 21, 1980 to William A. Trott discloses a self-inflating and self-cleaning catheter assembly which incorporates a selectively insertable auger assembly for removing blood clots. Because the auger assembly is exposed to the outside atmosphere before being introduced into the catheter, the risk of infection is increased. U.S. Pat. No. 4,762,130 issued Aug. 9, 1988 to Thomas J. Fogarty, Thomas B. Kinney and James C. Finn discloses a catheter with a corkscrew-like balloon. As in the Popa disclosure, the balloon in Fogarty et al. is used like a plunger, moving in and out of blood vessels to remove blood clots after the blood clots have been speared by the auger shape. Again, because at least portions of the controlling structure are exposed to the outside atmosphere, the chances of infection when the tube 10 is reintroduced into the body is increased. U.S. Pat. No. 4,954,129 issued Sep. 4, 1990 to David Giuliani and Gerald G. Vurek discloses a catheter arrangement which relies on the use of liquid flushing materials only to remove blood clots and other materials.

SUMMARY AND OBJECTS OF THE INVENTION

It is an object of this invention to provide a thrombus-mobilizing thoracostomy tube that is self-contained and effective to remove blood clots without increasing the chances of infection, thereby maintaining sterile conditions.

It is a further object of this invention to provide a thrombus-mobilizing thoracostomy tube which is effective to remove blood clots formed therein without exposing internal parts to the atmosphere outside of the body.

These and other objects are obtained by providing a thrombus-mobilizing thoracostomy tube with an elongated balloon located between the distal and proximal ends of the tube within the thoracic cavity, the tube also being provided with a plurality of fenestrations between the tube distal end and chest wall, to enable drainage of the thoracic cavity. The balloon is connected to a port for the introduction of air or other fluids so as to inflate the balloon. When a blood clot develops, the fenestrations become occluded, thereby preventing drainage of the thoracic cavity. When that occurs the balloon is inflated, the inflation being from the distal end of the balloon towards the proximal end of the balloon, the balloon pushing the clot before it towards the suction end of the tube outside the body. The tube also has an inlet port outside the body and an outlet port within the body near the proximal end of the balloon, through which a flushing liquid may be introduced into the tube between the proximal end of the balloon and the blood clot. The flushing liquid may be, for example, heparinized saline solution. Urokinase, an enzyme similar to streptokinase that is found in human urine and used to dissolve blood clots, may be used as an alternative flushing fluid that is thrombolytic, i.e. dissolves clots. Since the inflated balloon now covers the fenestrations, access thereto by the flushing liquid is denied. Instead, fluid pressure is built up between the inflated balloon and the clot to push the clot further towards the suction end of the tube, until finally the clot is removed from the tube. Thereafter the balloon is deflated and drainage once again can occur. Since the balloon is not moved back and forth as a plunger, no part of the thoracostomy tube is exposed to external contaminants and, accordingly, the risk of infection is substantially reduced. The use of thrombolytic flushing fluids is relatively inexpensive compared to the cost of inserting a new chest tube to replace one that has become useless due to blood clots.

Other objects, features and advantages of this invention will become apparent from the following detailed description and the appended claims, reference being had to the accompanying drawings forming a part of the specification, wherein like reference numerals designate corresponding parts of the several views.

BRIEF DESCRIPTION OF THE DRAWINGS

FIG. 1 shows a conventional prior art thoracostomy tube inserted into the thoracic cavity.

FIG. 2 is a cross-section view showing a blood clot formed within the conventional prior art thoracostomy tube of FIG. 1.

FIG. 3 is a cross-section view showing the thrombus-mobilizing thoracostomy tube of this invention.

FIG. 4 is a cross-section view of the thrombus-mobilizing thoracostomy tube taken along section line 4—4 of FIG. 3.

DETAILED DESCRIPTION OF THE PREFERRED EMBODIMENT

Figure 5:
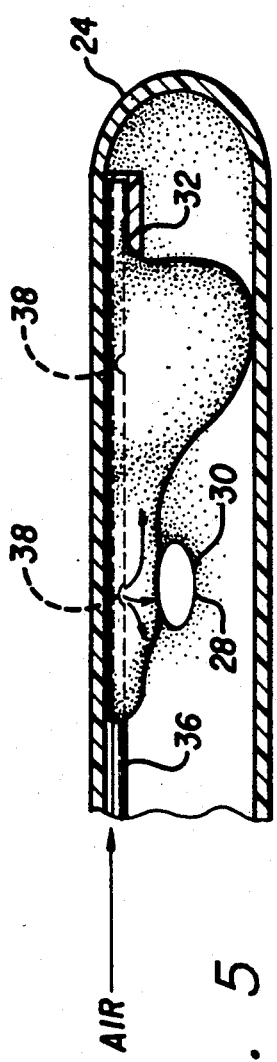
FIG. 5 is a cross-section view of the thrombus-mobilizing thoracostomy tube showing the progressive inflation of a balloon from the distal end thereof to the proximal end thereof.

Before explaining in detail the present invention it is to be understood that the invention is not limited in its application to the details of construction and arrangement of parts illustrated in the accompanying drawings, since the invention is capable of other embodiments and of being practiced or carried out in various ways. Also it is to be understood that the phraseology and terminology employed herein is for the purpose of description and not limitation.

FIG. 1 shows a conventional prior art thoracostomy tube 10 that has been introduced through an incision 12 in chest wall 14 into the thoracic cavity 16 for the purpose of draining blood and other fluids from thoracic cavity 16, which enter tube 10 through fenestrations or openings 18. Drainage of the blood and other fluids from the body through tube 10 is aided by the attachment of a conventional suction device 20 to tube 10 as shown in FIG. 1.

When a blood clot 22 forms within tube 10 as shown in FIG. 2, tube 10 becomes clogged and will not drain. Blood clot 22 cannot be dislodged or removed from tube 10 without removing tube 10 from chest wall 14. Such premature removal raises the risk of contamination when either the same tube 10 or a new tube 10 is reinserted through incision 12 into thoracic cavity 16 because of the exposure of tube 10 to the outside atmosphere or improper handling while outside of the body.

FIGS. 3, 4, 5 and 6 show the inventive thrombus-mobilizing thoracostomy tube 24 which substantially reduces the risk of contamination by enabling the dislodging and removal of a blood clot 26 without requiring that any part of the tube 24 be removed from the body.

As in the prior art, tube 24 is inserted through an incision 12 in chest wall 14 into thoracic cavity 16 for the purpose of draining blood and other fluids which enter tube 24 through fenestrations or openings 28. The end of tube 24 outside of the body is connected to a conventional suction device 20 in a manner similar to that shown in FIG. 1.

Incorporated in tube 24 is a latex balloon 30, suitably attached at its distal end to the tube 24 as at 32 and connected to an inlet port 34 by a first tube 36 which directs air or other inflating material into balloon 30 through ports 38. Also incorporated in tube 24 is an inlet port 40 connected by a second tube 42 to an exit port 44 enabling flushing fluids such as a heparin or saline solution to be introduced into tube 24. Urokinase may be used as an alternative flushing fluid that is thrombolytic.

Figure 6:
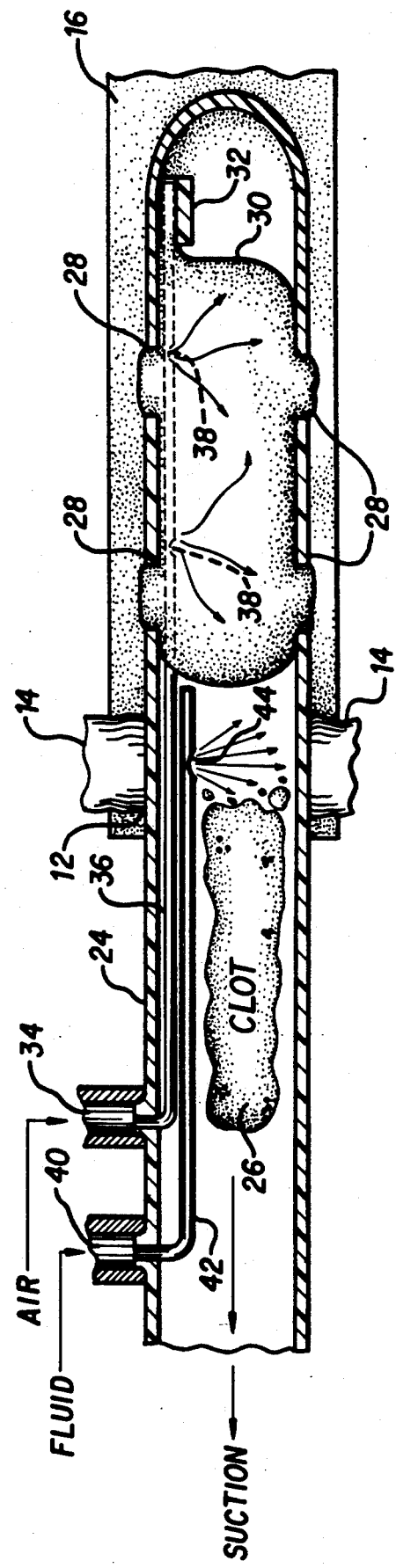
FIG. 6 is a cross-section view of the thrombus-mobilizing thoracostomy tube after the balloon has been fully inflated so as to dislodge a blood clot, showing the introduction of a flushing fluid to further force the blood clot towards the suction end of the tube.

FIG. 5 shows the manner in which balloon 30 inflates when air or another fluid is introduced through first tube 36, starting with the distal end of balloon 30 and progressing towards the proximal end of balloon 30 near the chest wall 14, as shown in FIG. 6. As balloon 30 inflates, it pushes against and dislodges blood clot 26, pushing blood clot 26 from the distal end of tube 24 towards chest wall 14. When balloon 30 is fully inflated, it occludes or blocks fenestrations or openings 28, thereby temporarily blocking drainage through fenestrations or openings 28. Subsequently, a flushing fluid, which may be a heparin, saline solution, or urokinase, is introduced through inlet port 40 and second tube 42. The flushing fluid exits second tube 42 at exit port 44, which is approximately located between balloon 30 and blood clots 26 at chest wall 14. The introduced fluid exerts pressure on blood clot 26 to move blood clot 26 towards the conventional suction device which removes clot 26 from tube 24. Subsequent to the removal of blood clot 26, balloon 30 is deflated by removing the air or other fluid therein through first tube 36 and port 34, thereby allowing drainage to resume through fenestrations or openings 28.

The removal of blood clots 26 from tube 24 is achieved without removing tube 24 from the body, thereby substantially reducing the risk of introducing contaminants into the body as in the prior art, when a tube 10 is reintroduced or replaced in the body. The system is self-contained and sterility is thereby maintained. The use of heparin solution aids in the removal process since heparin has the ability in certain circumstances to prevent the clotting of blood. Also, urokinase, an enzyme similar to streptokinase that is found in urine, aids in the removal process since it dissolves blood clots.

While it will be apparent that the preferred embodiment of the invention herein disclosed is well-calculated to fulfill the objects above-stated, it will be appreciated that the invention is susceptible to modification, variation and change without departing from the proper scope or fair meaning of the subjoined claims.

I claim:

1. A thrombus-mobilizing thoracostomy tube comprising:

an elongated tube means having a proximal end and a closed distal end inserted into a thoracic cavity in a user's body through a surgical incision in a chest wall, said elongated tube means including a plurality of fenestration means located near said closed distal end of said elongated tube means to enable drainage of blood and other fluids from said thoracic cavity;

balloon means disposed internally of said elongated tube means being attached to said elongated tube means at said closed distal end of said elongated tube means and inflatable from said closed distal end of said elongated tube means towards said proximal end of said elongated tube means so as to dislodge and move a blood clot when formed;

first tube means including a first inlet port means and a first outlet port means located within said elongated tube means and connected to said balloon means to enable said balloon means to be inflated; and second tube means including a second inlet port means and a second outlet port means located within said elongated tube means and extending to a proximal end of said balloon means, said second tube means for receiving a flushing fluid when said balloon means is inflated to enable said flushing fluid to be introduced into said elongated tube means between said inflated balloon means and said blood clot; whereby a blood clot when formed in said elongated tube means may be dislodged and flushed out of said elongated tube means without removing said elongated tube means from said user's body, thereby reducing the risk of contamination and maintaining a sterile condition.

2. A thrombus-mobilizing thoracostomy tube as in claim 1 wherein:

said balloon means when inflated occludes said fenestration means, thereby preventing drainage until said balloon means is deflated after said blood clot is flushed from said elongated tube means.

3. A thrombus-mobilizing thoracostomy tube as in claim 2 wherein:

said first tube means extends from said first inlet port means located outside of said user's body to said first outlet port means located within said balloon means, whereby a suitable means may be externally introduced to inflate said balloon means without removing any portion of said elongated tube means and first tube means from the user's body.

4. A thrombus-mobilizing thoracostomy tube as in claim 3 wherein:

said second tube means extends from said second inlet port means locatable outside said user's body adjacent said first inlet port means to said second outlet port means locatable within said user's body adjacent the proximal end of said balloon means when said balloon means is inflated, whereby said flushing fluid may be introduced between said inflated balloon means and said blood clot without removing any portion of said elongated tube means and said second tube means from the user's body.

5. A thrombus-mobilizing thoracostomy tube as in claim 4, further comprising a suction means connected to said elongated tube means at said proximal end locatable outside of said user's body whereby drainage of blood and other body fluids is enhanced.

6. A thrombus-mobilizing thoracostomy tube as in claim 5 wherein said flushing fluid comprises a heparin solution.

7. A thrombus-mobilizing thoracostomy tube as in claim 5 wherein said flushing fluid comprises a saline solution.

8. A thrombus-mobilizing thoracostomy tube as in claim 5 wherein said flushing fluid comprises a heparinized saline fluid.

9. A thrombus-mobilizing thoracostomy tube as in claim 5 wherein said flushing fluid comprises urokinase fluid.

* * * * *